United States Patent [19]

Forbes

[11] Patent Number: 5,794,623
[45] Date of Patent: Aug. 18, 1998

[54] INTRAMYOCARDIAL WENCKEBACH ACTIVITY DETECTOR

[75] Inventor: A. Dean Forbes, Palo Alto, Calif.

[73] Assignee: Hewlett-Packard Company, Palo Alto, Calif.

[21] Appl. No.: 722,351

[22] Filed: Sep. 27, 1996

[51] Int. Cl.$^6$ ........................................... A61B 5/0402
[52] U.S. Cl. ...................... 128/702; 128/901; 128/700
[58] Field of Search ........................... 128/671, 700, 128/702, 901; 600/483, 484, 513, 515

[56] References Cited

U.S. PATENT DOCUMENTS

| | | | |
|---|---|---|---|
| 3,587,562 | 6/1971 | Williams | 128/671 |
| 4,519,395 | 5/1985 | Hrushesky | 128/700 |
| 4,802,491 | 2/1989 | Cohen et al. | 128/702 |
| 5,003,976 | 4/1991 | Alt | 128/671 |
| 5,025,784 | 6/1991 | Shao et al. | 128/700 |
| 5,148,812 | 9/1992 | Verrier et al. | 128/704 |
| 5,187,657 | 2/1993 | Forbes | 364/413 |
| 5,188,116 | 2/1993 | Pommrehn | 128/696 |
| 5,265,617 | 11/1993 | Verrier et al. | 128/704 |
| 5,348,020 | 9/1994 | Hutson | 128/696 |
| 5,437,285 | 8/1995 | Verrier et al. | 128/702 |
| 5,474,078 | 12/1995 | Hutson | 128/699 |
| 5,503,160 | 4/1996 | Pering et al. | 128/706 |
| 5,511,554 | 4/1996 | Helfenbein et al. | 128/706 |

OTHER PUBLICATIONS

Virginia C. Klema et al., "The Singular Value Decomposition: Its Computation and Some Applications", 1980, vol. AC-25(2), pp. 164–176, *IEEE Trans. Automat. Contr.*

William H. Hutson, "High–Resolution Subspace Techniques for Cardiac Analysis", Oct. 24–26, 1995, vol. I, pp. 230–238, *Proceedings of the 6th International Conference on Signal Processing Applications & Tech*, Boston MA.

Ichiro Watanabe et al., "Two Types of ST–T Alternans During Acute Myocardial Ischemia in the In–situ Pig Heart", 1995, vol. 92(8), pp. I.–640, *Circulation*.

Richard T. Behrens, "Signal Processing Applications of Oblique Projection Operations", 1994, vol. 42(6), pp. 1413–1423, *IEEE Transactions on Signal Processing*.

Richard L. Verrier, "Electrophysiologic Basis for T Wave Alternans as an Index of Vulnerability to Ventricular Fibrillation", 1994, vol. 5(5), pp. 445–461, *Journal of Cardiovascular Electrophysiology*.

David S. Rosenbaum, et al., "Electrical Alternans and Vulnerability to Ventricular Arrhythmias", 1994, vol. 330(4), pp.235–241, *The New England Journal of Medicine*.

(List continued on next page.)

*Primary Examiner*—William E. Kamm
*Assistant Examiner*—Kennedy J. Schaetzle
*Attorney, Agent, or Firm*—Philip S. Yip

[57] ABSTRACT

An intramyocardial activity detector for detecting repeating patterns of irregular intramyocardial Wenckebach activity in the heart of a patient is provided. The apparatus includes a mechanism measuring electrocardiogram (ECG) signals from the body, a mechanism for measuring respiratory signals from the body, and a processor electrically associated with the two mechanisms means for measuring to determine the presence of intramyocardial Wenckebach activity of two or more phases. The processor calculates Wenckebach basis function strengths that indicate the presence of voltage in the measured ECG signals caused by repeating patterns of irregular intramyocardial Wenckebach activity via a relationship that describes the measured ECG signals as comprising Wenckebach input being additive to respiratory interference. In this relationship a nonsingular Wenckebach matrix W representing Wenckebach basis functions reflecting Wenckebach phases and a nonsingular interference matrix R act on the ECG signals to extract the Wenckebach input. The nonsingular interference matrix R based on the respiratory signals and the ECG signals of the patient represents how the measured ECG signals are related to the phases of the respiration. The Wenckebach basis function strengths are calculated in terms of the measured ECG signals, the nonsingular Wenckebach matrix W, and the nonsingular interference matrix R.

21 Claims, 7 Drawing Sheets

OTHER PUBLICATIONS

Alle–Jan Van Der Veen, et al., "Subspace–Based Signal Analysis Using Singular Value Decomposition", 1993, vol. 81(9), pp. 1277–1308, *Proceedings of the IEEE*.

William. H. Press, et al., *Numerical Recipes in C: The Art of Scientific Computation*, 2nd Ed., 1992, pp. 66, Cambridge University Press, Cambridge, MA.

John N. Amoore, et al., "Respiration and the ECG: A Study Using Body Surfaces Potential Maps", 1988, vol. 21(3), pp. 263–271, *Journal of Electrocardiology*.

D. Leigh Carson, et al., "Characterisation of Unipolar Waveform Alternation in Acutely Ischaemic Porcine Myocardium", 1986, vol. 20, pp. 521–527, *Cardiovascular Research*.

INTRAMYOCARDIAL WENCKEBACH ACTIVITY DETECTOR

FIELD OF THE INVENTION

The present invention is related to irregular myocardial activities of the heart of an animal, more particularly to the detection of Wenckebach activity.

BACKGROUND

Wenckebach Activity

Of the 400,000 sudden cardiac deaths (SCD) that occur in North America annually, sixty percent occur without any recognized warning. However, even among individuals in the top decile of risk, only a small percentage die due to sudden cardiac death each year. These potential SCD victims are indistinguishable from the rest of high risk individuals by present methods of analysis. Furthermore, a sizable majority of SCD victims (60%) are not even in the top decile of risk. There is currently no known way of targeting aggressive therapies at the small percentage of high risk subjects who will be SCD victims within a year.

SCD typically results from the interplay of three underlying factors: myocardial vulnerability, electrical instability, and neuroendocrine activation. The interplay of the three factors affects SCD occurrence. However, a single factor, depending on its strength, may in itself be enough to produce SCD.

Classically, risk factor analysis was used to identify those at elevated risk of SCD. In recent years, to improve SCD risk assessment, researchers have introduced purportedly direct measures of cardiovascular instability and related these to the incidence of SCD. Since most of the proposed measures focus on only one of the many factors underlying SCD, the raw measures provide (statistically) marginal analyses and hence tend to be inadequate for diagnostic purposes.

To some extent, improper test marginality can be overcome through the proper choice of the measurement context. For example, a patient recovering from a recent myocardial infarction will most likely have a pathologically heterogeneous myocardial vulnerability. Exercising that patient will superimpose neuroendocrine activation. The electrical instability factor can then be studied.

Experimental and simulation studies of myocardial cells predict that electrically compromised tissue may exhibit electrical activity that is not randomly responsive but involves periodically varying or periodically thwarted membrane action potentials. For this reason, complex, periodic variations in the QRS-complexes and in the T- and U-waves should be more directly related to electrical instability than are the variations analyzed by present methods, and therefore to the risk of SCD. Both ST-T alternans (secondary to ion-handling anomalies) and myocardial Wenckebach failure (secondary to a reduced cellular safety factor) have been studied as related to ventricular fibrillation. See, e.g., D. S. Rosenbaum et al., "Electrical Alternans and Vulnerability to Ventricular Arrhythmias," *NEJM* 330(4):1994, 235–241; R. L. Verrier and B. D. Nearing, "Electrophysiologic Basis for T Wave Alternans as an Index of Vulnerability to Ventricular Fibrillation," *J Cardiovasc Physiol* 5:445–461, 1994; I. Watanabe et al., "Two Types of ST-T Alternans During Acute Myocardial Ischemia in the In-Situ Pig Heart," *Circ* 92(8):I-640, 1995; and D. L. Carson et al., "Characterization of unipolar waveform alternation in acutely ischaemic porcine myocardium," *Cardiovasc Res* 20:521–527, 1986.

ST-T alternans involves voltage levels of the ST-T segments that switch between two values on successive beats: high ST-T, low ST-T, high ST-T, and so on. Myocardial Wenckebach activity (MWA) is more complex. In MWA, a group of beats will vary in quite complex ways only to be followed, when the Wenckebach activity is stable, by a next group of beats varying in just the same way. The nature of a simple, stable MWA is specified by a pair of integers, M:N. The first integer gives the periodicity of the MWA, i.e., how many trigger events occur before the cycle begins afresh; the second integer tells how many times the electrically compromised tissue responds when so triggered. Thus, for example, a 4:3 Wenckebach has a period of four beats with the tissue responding to three of the stimuli: respond, respond, respond, fail.

As a phenomenon, ST-T alternans is simply an ST-T localized mimic of 2:1 Wenckebach activity. Hence, a technique that can detect a M:N Wenckebach activity can also detect alternans. The Wenckebach activity perturbs the ECG potentials measured at the body surface. However, detecting intramyocardial Wenckebach activities from ECG signals is difficult, since the surface potentials will also be contaminated by superimposed muscle tremor noise (EMG), electromagnetic interference (EMI), and interference due to respiration and due to variations in cardiac filling. Further confusing matters are the facts that a given region of the heart may be mode-hopping in time from one Wenckebach pattern to another and that various regions of the heart may be exhibiting disparate, even competing, Wenckebach patterns.

Investigation of alternans activity (as it relates to susceptibility to sudden cardiac death) has been reported by two university groups: Massachusetts Institute of Technology (NIT) and Georgetown University. See, e.g., D. S. Rosenbaum et al., Supra.; U.S. Pat. No. 4,802,491; U.S. Pat. No. 5,148,812; and U.S. Pat. No. 5,437,285. In the MIT method, the incidence and extent of T-wave alternans was estimated by steps including forming a spatial magnitude vector, identifying and aligning 128 T-waves each of 150 msec duration, and Fast Fourier transforming (FFT) each epoch of the T-waves. One drawback of this technique is that the processing is labor-intensive. In the Georgetown method, data were analyzed via the method of complex demodulation. The Georgetown group attributes T-wave alternation to the cellular monophasic action potential duration alternans phenomenon, not to gap junction failure (the mechanism originally put forward by the MIT group). However, neither the MIT spectral approach nor the Georgetown complex demodulation approach is suited to the detection of mixtures of Wenckebach activity.

Subspace Filtering Methodology

When modern signal analysts are required to extract a subtle signal from a timeseries corrupted by interference and noise, a useful technique is "subspace filtering." See, e.g., V. C. Klema and A. J. Laub, "The Singular Value Decomposition: Its Computation and Some Applications," *IEEE Trans AC* 25 (2):164–176, 1980; A-J van der Veen et al., "Subspace-Based Signal Analysis Using Singular Value Decomposition," *Proc IEEE* 81 (9):1277–1308, 1993.

In subspace filtering, a given timeseries is viewed as a vector in an multi-dimensional space. The technique seeks to determine a subspace that contains the signal part of the timeseries while being orthogonal to the interference and noise. The basis vectors of the full vector space, as well as its subspaces, are typically determined using linear algebra's well-known method of singular value decomposition (SVD). Expanded in terms of the basis vectors of the signal subspace, the signal emerges from the obscuring interference and noise.

Subspace filtering for compression of the ECG was investigated more than two decades ago. It was assumed that the basis vectors corresponding to the smallest singular values would correspond to noise. Recently, W. H. Hutson applied subspace filtering methods to ECG signals by suppressing interference to detect both alternans and late potentials. See W. H. Hutson, "High-Resolution Subspace Techniques for Cardiac Analysis," *Proceedings of the Int. Conf. On Sig. Proc. Appl. and Tech.* 1995:230–238; and W. H. Huston, U.S. Pat. No. 5,474,078. However, no subspace analysis has been applied to the Wenckebach activity, which is much more complex than alternans.

SUMMARY

In the present invention, an apparatus for detecting repeating patterns of irregular intramyocardial activity is provided. The apparatus includes a device for measuring electrocardiographic (ECG) signals; a device for measuring respiratory signals; and a processor adapted to numerically reduce the interference on the measured ECG signals, based on the measured respiratory signals. In a preferred system, to determine the presence of repeating patterns of irregular intramyocardial activity, the processor is adapted to reduce the interfering effect of respiration by having data of a nonsingular Wenckebach matrix W in the processor; forming a nonsingular respiratory matrix R describing the respiratory signals (e.g., respiratory impedance signals); and calculating the Wenckebach phase strength based on the nonsingular Wenckebach matrix W, the nonsingular respiratory matrix R and the sensed ECG signals. Preferably, the nonsingular Wenckebach matrix W is obtained by orthogonalizing a singular Wenckebach matrix W corresponding to the Wenckebach phases for a number of cardiac beats. The respiratory matrix R reflects the respiratory signals during the cardiac beats.

The present invention allows detection of elaborate mixtures of Wenckebach periodicities. It can also be used to detect alternans, since an alternans pattern mimics the simplest of the Wenckebach patterns, albeit during only part of the ST-T segment. The present invention provides a technique suitable for detecting alternans as well as non-alternan type of intramyocardial Wenckebach activity. Since not all electrical instabilities are alternans, the technique of the present invention is advantageous over prior art methods for detecting alternans.

Because the method operates in the time domain, robust methods that can be used for inferring the Wenckebach phase strengths are readily available, e.g., the Penrose-Moore generalized inverse (corresponding to least squares and solution) and other inverses (corresponding to least-one-norm solution, etc.) are available. Because the technique of the present invention operates in the time domain, censoring of bad or inappropriate data is relatively straightforward. This is advantageous because anomalous beats introduce great mathematical difficulties into frequency-domain methods. Furthermore, contrary to previous methods for analyzing anomalous cardiac beats, the present invention does not assume that the respiratory interference and noise are orthogonal to the cardiac signals of interest. Instead, obliqueness of the spaces having the signals of interest is explicitly treated. Since the cardiac signals and interference-noise are in fact nonorthogonal, the present invention gives more accurate results than previous methods. Preferably, the nature and extent of respiratory interference is not inferred directly from the ECG data, thus avoiding the risk of obscuring certain desired signals while removing the interference. Instead, the properties of the respiratory interference are extracted by careful analysis of respiratory signals measured independently from the ECG signals.

In a preferred environment, beats that occur during model-violating (i.e., outside specific limits) breaths are identified and censored from the data, as are noisy or otherwise anomalous beats with anomaly outside a selected limit. This permits the Wenckebach signals to be more reliably detected, thereby providing useful information on irregular intramyocardial activity and the prediction of SCD.

BRIEF DESCRIPTION OF THE DRAWINGS

The following figures are included to better illustrate the embodiments of the apparatus and technique of the present invention. In these figures, like numerals represent like features in the several views.

DETAILED DESCRIPTION OF THE INVENTION

Figure 1:
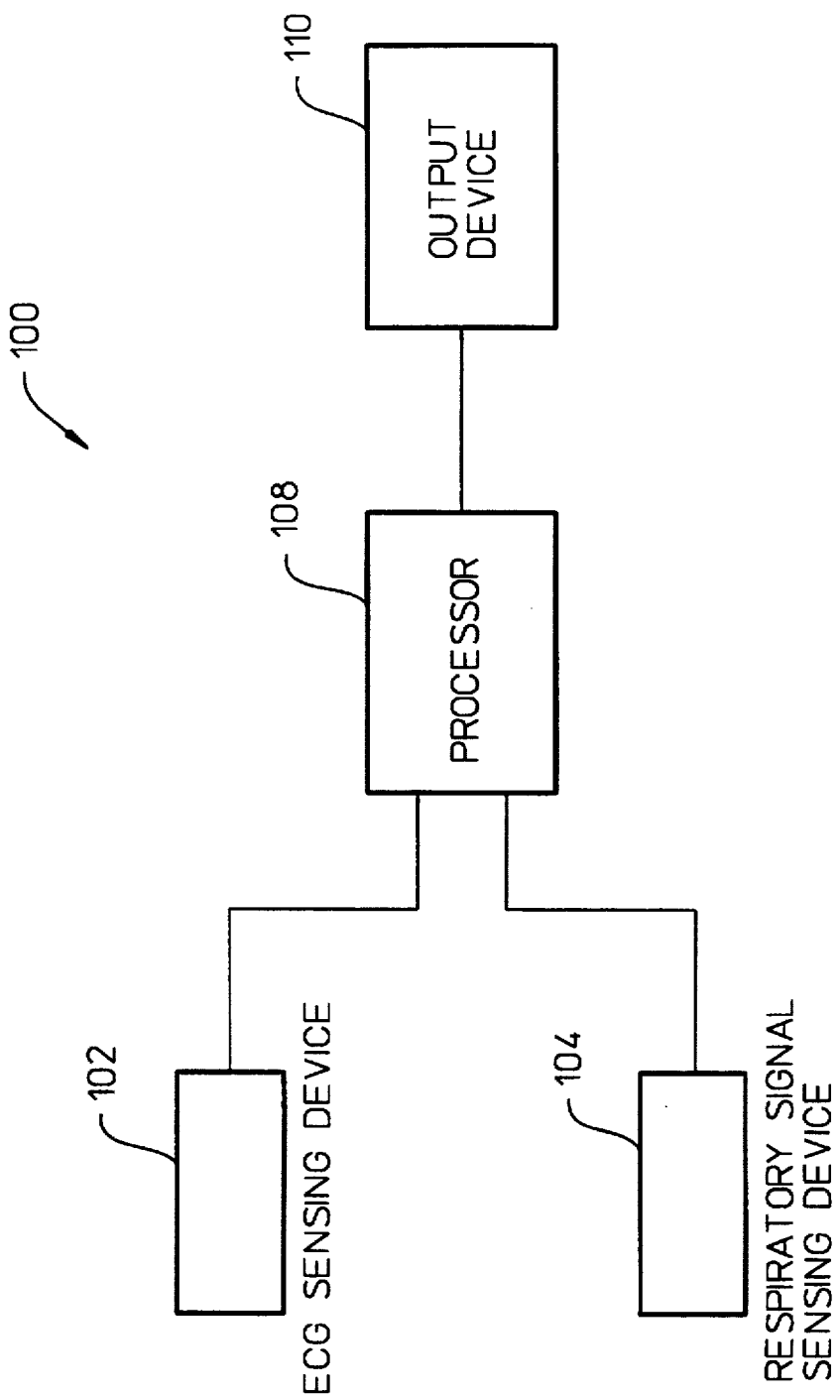
FIG. 1 shows an embodiment of the apparatus of the present invention.

FIG. 1 shows an embodiment of the apparatus of the present invention for detecting repeating (or cyclical) irregular intramyocardial activity. As used herein, the term "irregular intramyocardial activity" refers to the failure of intramyocardial tissue to respond to every triggering stimulus, which is usually regular and periodic. In "repeating" or "cyclical" irregular intramyocardial activity, the pattern of response and failure to respond to triggering stimuli repeats over time in a periodic fashion.

In FIG. 1, the apparatus 100 includes a device 102 for sensing, i.e., measuring, ECG signals and a device 104 for sensing, i.e., measuring, respiratory signals. For present purposes, transthoracic respiratory impedance (RI) is used as an illustrative example of respiratory signals. An alternative indicator of respiration might be used, e.g., nasal thermistor, strain gauge on the chest, and the like. Methods commonly used for measuring respiratory signals can be used. The ECG signal-sensing device 102 and the RI signal-sensing device 104 are electrically connected to a processor 108 for processing the signals from the devices 102 and 104. Devices for sensing ECG and RI signals are widely known in the art. Examples of such devices include ECG electrodes and RI electrodes which can be positioned at appropriate locations on a patient. If preferred, the RI electrodes can be the same electrodes that measure the ECG signals, except that a higher frequency current is injected in the RI to result in the voltage of the RI signals. The signals from the electrodes can be passed through amplifier(s) before being processed by the processor 108. Alternatively, the processor can have amplifier(s) for amplifying the signals. Also, analog or digital filters can be used for filtering noise before processing signals with the processor 108. The processor 108 can be an electronic digital computer, neural network computer, microprocessor, and the like, that has memory for storing data and can perform matrix operations. Preferably, there is an output or display device 110 such as printer, CRT display, plotter, and the like, for interfacing with a human operator. The algorithm for calculating the matrix operations or for determining the extent of the Wenckebach activity from the ECG and RI signals can be stored in the processor or imported (or read) into the processor by means of electrical wires and storage devices such as hard disks, floppy disks, magnetic tapes, and the like.

This invention detects repeated patterns of irregular intramyocardial activity by appropriately projecting ECG signals (data) onto a Wenckebach subspace to remove the interfering effect of respiration. To facilitate the understanding of the present invention, the detection approach is first described assuming orthogonality of the subspaces. Because the subspaces often are, in fact, oblique, the detection approach is then reformulated to solve the detection problem using oblique projection. However, to use matrices to solve for values of variables, the question of singularity of the matrices is first addressed.

Singularity of the Original Wenckebach Matrix

Figure 2A:
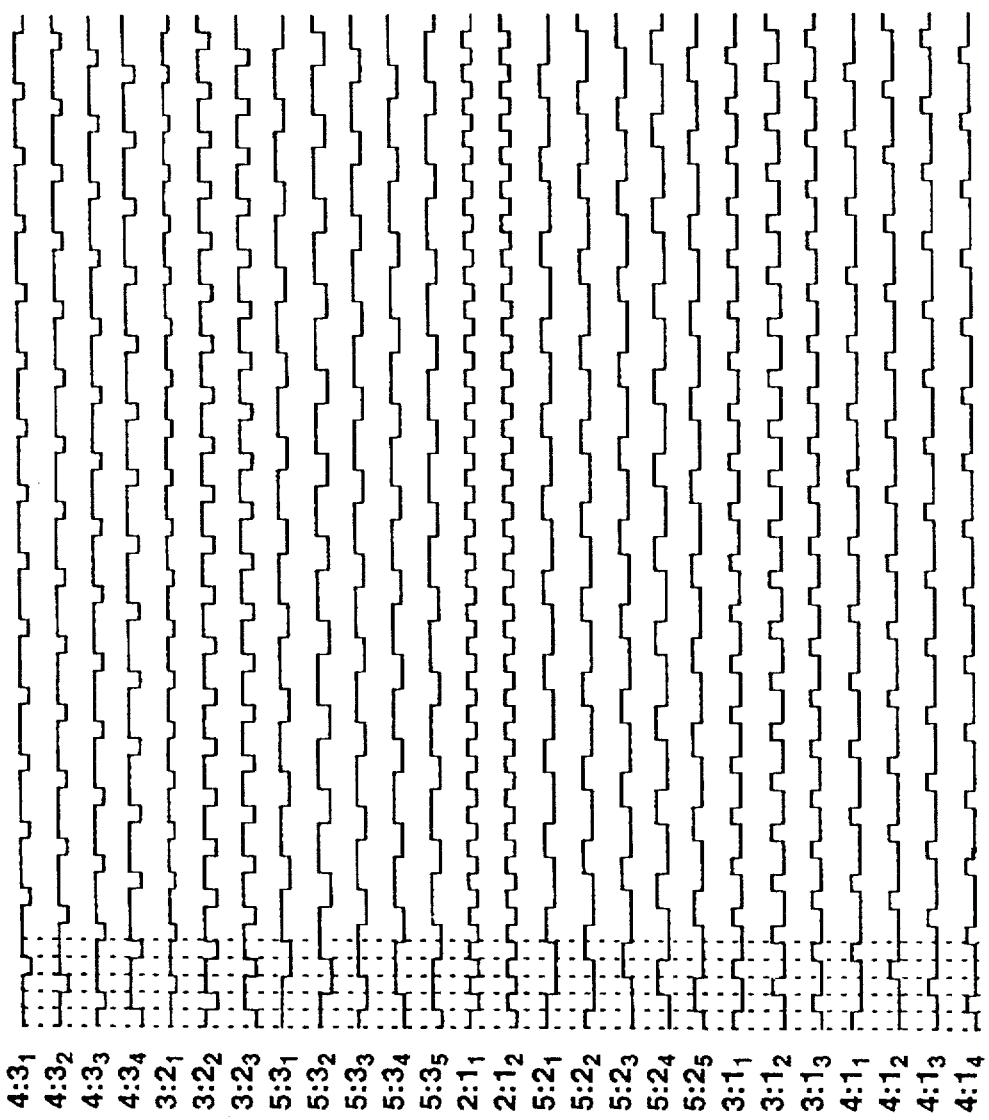
FIG. 2A shows the phases associated with Wenckebach modes; in this example, seven Wenckebach modes are shown over 60 beats.

FIG. 2A shows the 26 phases associated with seven Wenckebach modes over 60 beats. These seven modes represent the most significant Wenckebach modes, although, if desired, a person skilled in the art can, based on the present disclosure, use a larger or smaller number of Wenckebach modes, phases, and beats in an analysis similar to the present illustration and the subsequent description of the invention. In FIG. 2A, each phase switches between unit strength, if the involved tissue responds to a trigger event (i.e., stimulus or cardiac activation beat), and zero strength if the tissue does not respond. The dashed vertical lines delimit, starting from the far left, the first through fifth beats. The symbols 4:3, 3:2, 5:3, 2:1, etc. are the Wenckebach modes. The subscripts associated with a mode show the phases associated with that particular mode. The top tracing shows the $4:3_1$ phase, which consists of cycles of three responses followed by a non-response. The 4 represents the number of beats (i.e., trigger events) in each cycle of the 4:3 mode. The 3 represents the number of responses in the 4:3 mode. The phases, identified by the subscripts, e.g., $_1$, $_2$, etc., represent the variations in the 4:3 mode, due to the differences in the time of detection. For example, the second tracing from the top shows the $4:3_2$ phase, which consists of cycles of two responses, followed by a non-response and then a response. The other modes can be similarly interpreted.

The 26 phases shown in FIG. 2A represent the phases believed to be the most often encountered. The modes appear in order of decreasing activation ratio (0.75, 0.67, 0.60, 0.50, 0.40, 0.33, 0.25). In effect, FIG. 2A defines a $\{n_w \times n_b\}$ transposed Wenckebach matrix of ones (1), representing tissue responses, and zeros (0), representing tissue nonresponses, i.e., failure to respond. If we let each Wenckebach phase (each tracing) of FIG. 2A generate a column in a descriptive matrix $\tilde{W}$ so that the successive rows of the matrix correspond to successive beats, then, as an example, an eight-beat by 26-phase matrix, $\tilde{W}$, will look like the following:

$$\tilde{W} = \begin{bmatrix} 11101101110010110001001000 \\ 11011011100101100010010001 \\ 10110111001110000110100010 \\ 01111100011101001101000100 \\ 11101010111010011000011000 \\ 11010111110001110000100001 \\ 10111101100110100011000010 \\ 01111011001101000110011100 \end{bmatrix}$$

In a Wenckebach matrix, $\tilde{W}$ of $\{n_b \times n_w\}$ size, $n_b$ is the number of beats and $n_w$ is the number of phases. To see how this matrix is used, let us first consider a situation where only one region is exhibiting one sort of Wenckebach behavior at one time after the onset of the QRS-complexes. Let the potential difference between two points on the body surface due to a small region, when it is responsive to triggering, be $x_i$, where i is an index telling which Wenckebach phase we are dealing with. For illustration, suppose that the small region is exhibiting the first Wenckebach pattern in FIG. 2A (i.e., phase $4:3_1$, having responses of: on, on, on, off). Let the potential difference produced when the region is responsive be $x_1$. Since we are supposing that only this one region is exhibiting Wenckebach activity at this time during the QRS-complexes, we may define this simple $\{26 \times 1\}$ source-strength vector x as:

$$x = \begin{bmatrix} x_1 \\ 0 \\ 0 \\ \cdot \\ \cdot \\ \cdot \\ 0 \\ 0 \end{bmatrix}$$

Let us define a vector of beat-by-beat ECG potentials as b. For illustration, assume we are looking at the first eight beats, then b is an $\{8 \times 1\}$ vector. For the present very simple case with a $4:3_1$ phase, given for illustrative purposes, the first eight beat voltages will be given by:

$$b = \begin{bmatrix} x_1 \\ x_1 \\ x_1 \\ 0 \\ x_1 \\ x_1 \\ x_1 \\ 0 \end{bmatrix}$$

The matrix $\tilde{W}$ and vectors x and b are related by:

$$\tilde{W}x = b \qquad \text{Eq. 1}$$

This relation is valid when any or all of the various Wenckebach phases are active. We measure the voltages b and by that infer whether Wenckebach activity exists and determine the strength (i.e., the significance) of each phase. If x is found to be larger than a chosen limit, i.e., sufficiently far from zero, Wenckebach activity can be considered to exist. The solution may be written:

$$x = \tilde{W}^I b \qquad \text{Eq. 2}$$

where $\tilde{W}^I$ is a generalized inverse of $\tilde{W}$.

It is important to note that FIG. 2A is a pictorial representation of the transpose of a "singular" Wenckebach matrix. That the underlying matrix is singular can be appreciated by noting that the sum of the phases making up each Wenckebach mode is a constant. Hence, the rows of FIG. 2A (columns of the corresponding $\tilde{W}$) are linearly dependent, making the matrix singular. FIG. 2A also reveals that for each phase in the top half of the figure a phase in the lower half exists such that the pair sums to a row of ones, also indicating singularity.

Figure 2B:
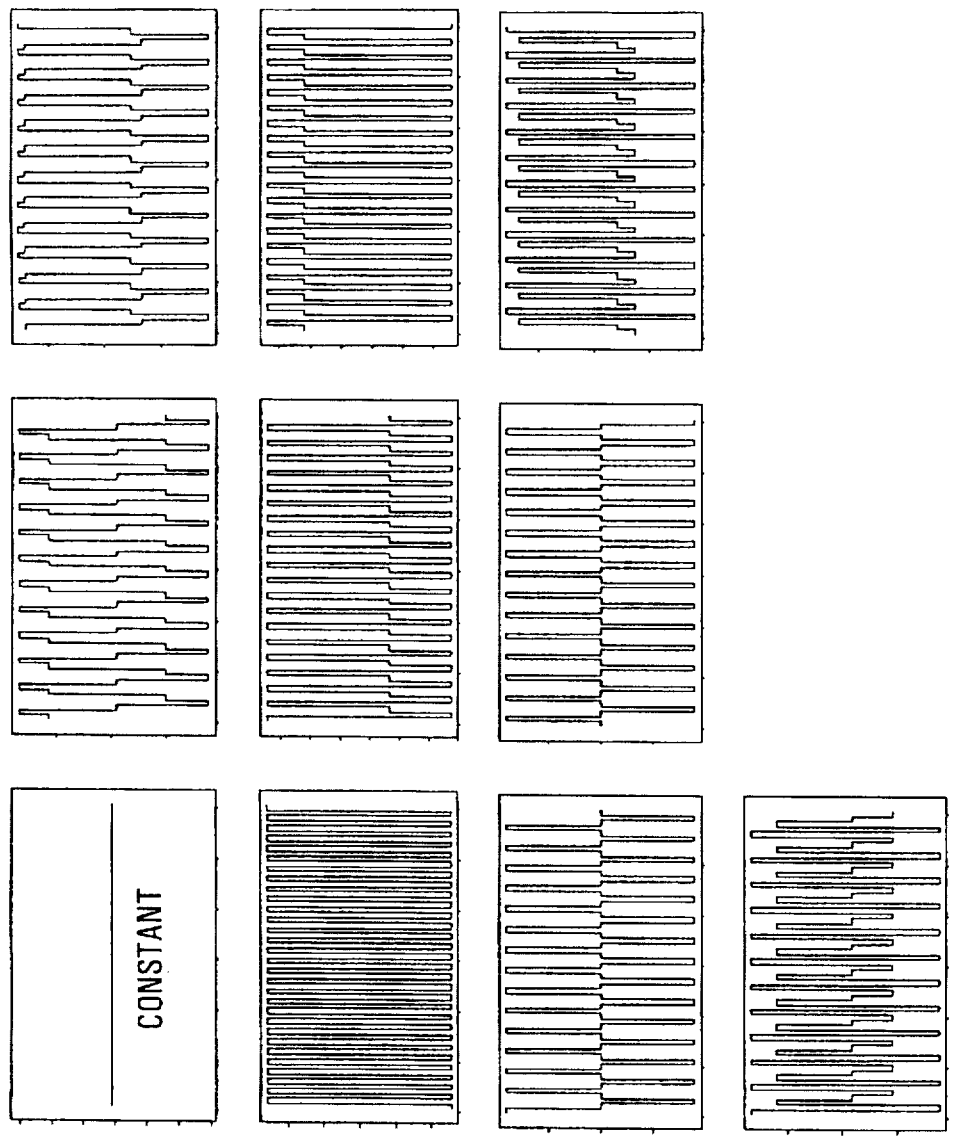
FIG. 2B shows the basis functions associated with Wenckebach phases of FIG. 2A after orthogonalization.

To detect the presence of Wenckebach activity, a well-conditioned system matrix, i.e., a matrix without singularity, is needed. The Gram-Schmidt orthogonalization procedure allows this to be achieved. However, the numerical stability of the original Gram-Schmidt procedure is quite poor. Consequently, we use singular value decomposition to achieve our goal. (See W. H. Press et al., Numerical Recipes in C: The Art of Scientific Computation, Second Edition, Cambridge, Cambridge University Press, 1992, 66, which is incorporated by reference herein). When we orthogonalize the basis functions that describe the waves (i.e., curves in the rows) of FIG. 2A, we obtain 26 new basis functions, the first ten of which are shown in FIG. 2B. For clarity, the units of the graphs in FIG. 2B are not shown. The abscissa shows time, and the ordinate shows amplitude. We also find that singular values associated with basis functions 11 through 26 (i.e., associated with the basis functions representing Wenckebach phases 11 through 26) are zero, indicating the very extensive singularity of the original Wenckebach matrix. Basis functions are a set of functions, linear combinations of which approximate other functions. A well-known example of basis functions are the sines and cosines used in Fourier analysis to expand functions as Fourier series—sums of appropriately weighted sines and cosines. Given our Wenckebach phases of the original $\tilde{W}$ matrix, the Gram-Schmidt orthogonalization process is used to determine a set of uncorrelated basis functions in terms of which any of the original Wenckebach phases may be efficiently represented. In this illustrative example, to avoid singularity, we discard basis functions 11 through 26 obtained by orthogonalization, thereby forming a "probe matrix," a well-conditioned, orthogonalized $\{n_b \times 9\}$ matrix designed for the detection of the presence of Wenckebach activity. Estimation of individual Wenckebach phase strengths can follow after the detection of the existence of Wenckebach activity.

In our analysis technique, the interval-by-interval data making up the ECG data vector b are scaled to be zero mean. This allows the constant basis function, corresponding to monotonously repetitious activity, to be omitted. In other words, the repetitive voltage that occurs at every beat, i.e. the normal ECG voltage variation that occurs at every beat, is removed. Hereinafter, the measured data b refers to zero-meaned data unless specified to be otherwise.

Reformulating the Wenckebach Detection Problem to Make It Solvable

The original 26 Wenckebach phases are combined to form nine composite phases—basis functions—that span the Wenckebach space without linear dependence. "Spanning the Wenckebach space" means that an appropriate linear combination of the basis functions can synthesize each of the original Wenckebach phases. For example, a weighted sum and a weighted difference of the first and fourth basis functions yields the two phases making up the 2:1 mode. In FIG. 2B, the fourth basis function has period two and the first basis function provides the constant needed to shift the scaled fourth basis function to produce the 0-1 behavior of the 2:1 phases.

The basis vectors, when placed side-by-side, make up a nonsingular matrix, W, which is derived from the singular Wenckebach matrix, $\tilde{W}$, above. For the sake of clarity, W will be used hereinafter to represent the orthogonalized, nonsingular Wenckebach matrix. This nonsingular matrix is used to solve for the vector x giving the Wenckebach basis function strengths.

Because the process of constructing the basis vectors yields orthogonal vectors, the associated matrix will be nonsingular. In terms of the transformed matrix, the vector of Wenckebach strengths derived from the ECG measurements becomes:

$$x = W^I b \qquad \text{Eq. 3}$$

The elements of x now correspond to the various basis vectors (of composite Wenckebach phases), but Wenckebach activity will still exist only when x is non-zero. (Put differently, the x in this new solvable equation is different from the x in the old unsolvable equation, in which the Wenckebach matrix is singular, but the condition for the existence of Wenckebach activity remains that the magnitude of x is significantly nonzero.)

Signal Estimation in an Orthogonal Signal, Interference, and Noise Vector Space

Figure 3:
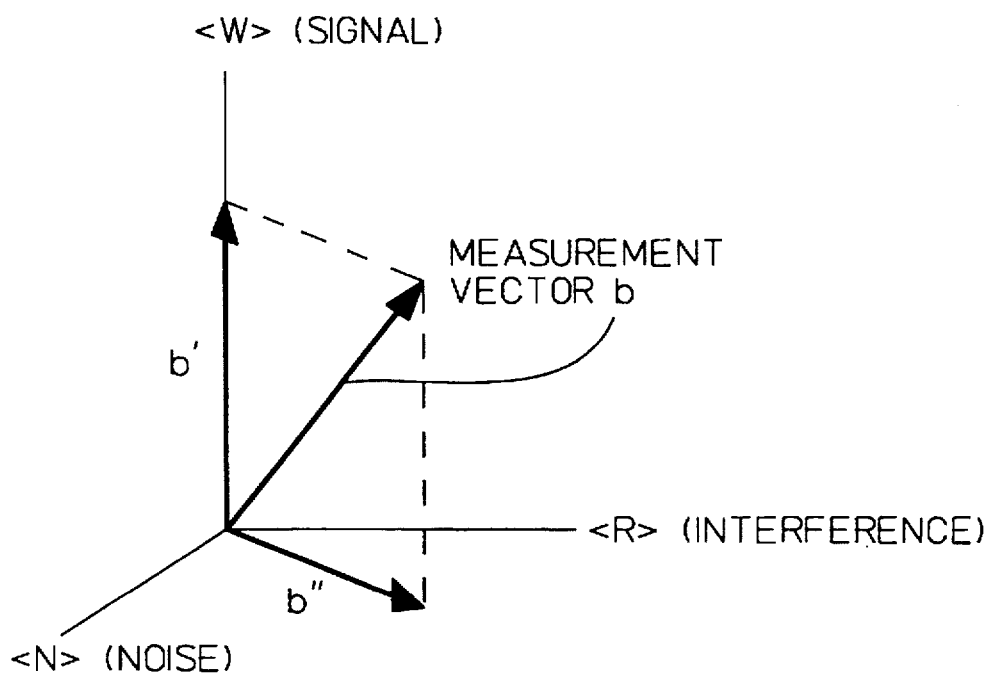
FIG. 3 shows an ECG measurement vector situated in an orthogonal Wenckebach-signal, interference, and noise vector space.

As mentioned previously, the ECG signal may be contaminated with interference due to respiration and noise. Hereinafter, the structured electrical interference due to respiration is referred to as "interference" and the random electrical noise, including electrical noise due to electromagnetic interference and muscle tremor, are referred to as "noise." To facilitate understanding of the present invention, we assume initially that the three Wenckebach-Signal/Interference/Noise vector subspaces are mutually orthogonal, i.e., they are totally independent from each other. This simplification is acceptable in that, with it, the technique of the present invention is applicable in detecting Wenckebach activities. The simplified vector space is illustrated in FIG. 3. In FIG. 3, <W> is the subspace (i.e., axis) for the Wenckebach signal, <R> is the subspace for the respiratory interference, and <N> is the subspace for the noise.

With the assumption that the subspaces are orthogonal, we can recover the Wenckebach signal from the measurement vector (represented by b) by projecting the measurement vector onto the Wenckebach signal subspace <W>. The vector b' represents the projection of b on the subspace <W>. The vector b" is the projection of b on the <N> and <R> subspaces, i.e., the subspaces of noise and interference, respectively. The mathematical procedure for so doing is the following.

Let:

W be the $\{n_b \times n_w\}$ orthogonalized Wenckebach matrix, b be a $\{n_b \times 1\}$ vector of measurements (data) of ECG signals, and x be the corresponding $\{n_w \times 1\}$ vector of Wenckebach basis function strengths.

The values of the components in the x vector represent the strengths (or magnitude) of the various particular Wenckebach basis functions.

W is a matrix whose columns span the Wenckebach-signal subspace <W>. It has $n_b$ rows, corresponding to $n_b$ beats, and $n_w$ columns, corresponding to Wenckebach basis functions, which describe the variety of Wenckebach modes. The component of b lying in the <W> subspace, $b_w$, is given in terms of the pseudo-inverse of W (represented by $W'$):

$$b_w = P_w b = WW'b \qquad \text{Eq. 4}$$

where $P_w$ is the projection matrix onto <W>.

Since $Wx=b_w$ and since $W'W=I$, $$x = W'WW'b = W'b \qquad \text{Eq. 5}$$

Thus, we see that if the signal subspace <W> is orthogonal to the respiratory interference subspace <R> and noise subspace <N>, then the vector of basis function strengths, x, is just the generalized inverse of the Wenckebach matrix $W'$ times the measurement vector b. Thus, when we solve a system via the generalized inverse, we are implicitly assuming that the interference and noise subspaces, <R> and <N>, respectively, are orthogonal to the Wenckebach signal subspace, <W>.

At a glance, the above approach assuming orthogonality between the subspaces seems satisfactory. However, we have found that the subspaces are, in fact, not orthogonal. Using orthogonal projection to solve for the overall Root Means Square Wenckebach signal strength from the ECG data b of normal subjects results in non-zero Wenckebach activity, peaking in QRS. Since no Wenckebach activity is expected in unstressed normal subject, this result indicates that the signal subspace is not orthogonal to the interference and/or noise subspaces. In other words, there is leakage from the interference or noise subspaces into the solutions for the Wenckebach signal strengths. The zero-mean vector b consists of components due to Wenckebach activity, tremor noise (EMG), electromagnetic interference (EMI), electrogastric interference (EEG), and respirational interference.

Preferably, the EMI and the electrogastric interference are suppressed by applicable techniques. Then our ability to determine the strengths of the Wenckebach basis functions will primarily be affected by the substantial interfering effects of respiration. When respiration is shallow, the effects of cardiac signals, tremor noise, and respiratory interference may be taken to be additive.

The Oblique Wenckebach Signal/Interference/Noise Vector Space

Figure 4:
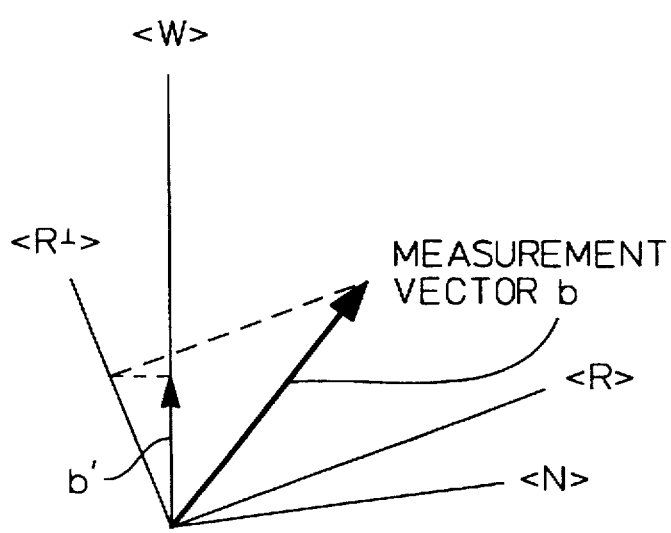
FIG. 4 shows an ECG measurement vector situated in an oblique Wenckebach-signal, interference, and noise vector space.

As previously stated, evidence shows that the Wenckebach signal, noise, and interference subspaces are not orthogonal, but are, instead, oblique. FIG. 4 shows an ECG measurement vector situated in oblique Wenckebach-signal, interference, and noise subspaces. In addition to the interference subspace <R>, we also show the orthogonal complement of the interference subspace <R$^\perp$>, which is orthogonal to the interference subspace <R>. As is indicated by the dashed lines in FIG. 4, estimation of the vector of Wenckebach basis function strengths proceeds by first projecting the measurement vector b on to the orthogonal complement <R$^\perp$> of the interference subspace <R>, thereby suppressing interference effects, and then projecting the resultant onto the Wenckebach subspace <W>.

The foregoing process is mathematically expressed as follows.

Let:

b be a $\{n_b \times 1\}$ vector of measurements (ECG data),

W be the $\{n_b \times n_w\}$ orthogonalized Wenckebach matrix spanning subspace <W>

R be a $\{n_b \times n_r\}$ matrix whose columns span the interference subspace, R, x be the $\{n_w \times 1\}$ vector of Wenckebach basis function strengths, y be the $\{n_r \times 1\}$ vector of respiratory phase strengths, and R$^\perp$ be a matrix spanning the orthogonal complement, <R$^\perp$>, of the interference subspace, <R>.

The components of x, as described before relating to FIG. 2B, reflect the strengths of the Wenckebach basis functions. The components of y show the strengths (i.e., magnitude) of the respiratory interference signals. Since the observed ECG signals (having the monotonously repetitive components removed) are the result of the combination of the Wenckebach input, the respiratory interference, and noise, we adopt the following additive, linear signal model:

$$b = [WR]\begin{bmatrix}x\\y\end{bmatrix} + \epsilon \qquad \text{Eq. 6}$$

where $\epsilon$ is $\{n_b \times 1\}$ additive (muscle tremor and phase-randomized EMI) noise. The respiratory interference is linearly additive to the Wenckebach signal for the case of normal, fairly shallow, respiration. (See Appendix.) Under this linear model, it can be shown that the estimate of the optimal strength (in the least squares sense) of the Wenckebach signal vector is given by (see, R. T. Behrens and L. L. Scharf, "Signal Processing Applications of Oblique Projection Operators," *IEEE Trans* SP 42(6):1413–1424, 1994):

$$x = W' E_{WR} b \qquad \text{Eq. 7}$$

where $E_{WR}$ is the oblique projection operator whose range space is <W> and whose null space is <R>.

The overall solution, of Equation 7 in terms of the Penrose-Moore generalized inverse of the combined WR matrix is:

$$\begin{bmatrix}x\\y\end{bmatrix} = [WR]'b \qquad \text{Eq. 8}$$

Following Behrens and Scharf, to solve the basic equation using the Penrose-Moore generalized inverse in block form, we obtain:

$$\begin{bmatrix}x\\y\end{bmatrix} = [WR]'b = ([WR]^T[WR])^{-1}[WR]^Tb = \begin{bmatrix}W^TWW^TR\\R^TWR^TR\end{bmatrix}^{-1}\begin{bmatrix}W^T\\R^T\end{bmatrix}b \qquad \text{Eq. 9}$$

Using the inversion formula for block matrices, we can extract the Wenckebach signal part x of the solution by introducing projection matrices:

$$x = (W^TW)^{-1} W^T(I - R(R^TP_w\perp R)^{-1}R^TP_w\perp)b = (P_r\perp W)'b \qquad \text{Eq. 10}$$

where $P_w\perp$ is the projection matrix onto the orthogonal complement of the signal space defined by:

$$P_w\perp = I - P_w = I - WW' \qquad \text{Eq. 11}$$

and $P_R\perp$ is the projection matrix onto the orthogonal complement of the interference space defined by:

$$P_R\perp = I - P_R = I - RR' \qquad \text{Eq. 12}$$

To estimate the Wenckebach basis function strengths via oblique projections, we must estimate R, a matrix whose columns span the interference subspace, <R>.

Matrix Spanning the Respiratory Interference Subspace

Under our additive linear model, a vector of respiratory interference strengths y is pre-multiplied by a matrix of interference transfer coefficients R with a size of $\{n_b \times n_r\}$ to produce a vector of beat-by-beat interference values (voltages). We assume that the degree of interference is directly related to the phase of respiration (i.e. in what part of a respiration cycle) and divide each respiration cycle into respiratory classes. The matrix R has as columns a set $(n_r)$ of the respiratory classes. Each epoch of each beat is associated with the respiratory phase during which that epoch occurs. Each row in R, corresponding to each beat, will have all of its entries equal to zero except for the entry in the column corresponding to the appropriate respiratory phase, which will be unity.

Figure 5:
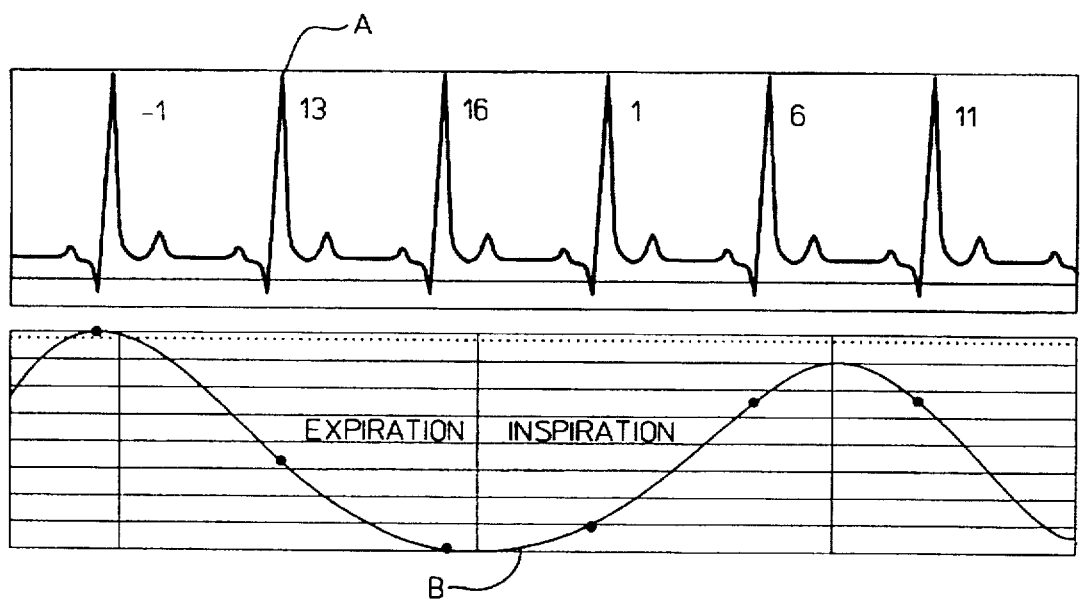
FIG. 5 are graphs showing how the ECG beats are associated with respiratory classes.

We have devised several technique for generating a matrix that spans the respiratory interference subspace. One such technique can be understood with reference to FIG. 5. In FIG. 5, curve A represents the ECG tracing and curve B represents the respiratory impedance (RI) tracing. The technique is as follows:

1. Remove the cardiogenic artifact from the RI signal, e.g. by using Physiological Event Time Averaging (PETA) filter, (See: R. D. Pering et al., U.S. Pat. No. 5,503,160 and US Pat. No. 5,511,554.)
2. Locate the maxima and the minima of the RI signal.
3. Detrend the RI signal by clamping the minima to zero.
4. Determine the $q^{th}$ decile of the peaks, e.g. using the $q^{th}$ decile.
5. Divide the range from zero up to the $q^{th}$ decile into M/2 equal intervals.
6. A beat whose QRS onset occurs during inspiration is assigned an appropriate class from the first half of those available. A beat whose QRS onset occurs during expiration is assigned an appropriate class from the second half of those available.

Any beat lying above the $q^{th}$ decile is assigned rejected respiratory class-1, since it is a breath too large for the small angle approximations, and hence, for additive model-to hold. As an illustration, in FIG. 5, M=16 can be used, i.e., there are 16 classes. Beats occurring during inspiration receive differing classes from beats occurring at comparable RI levels during expiration because of differing cardiac filling obtained between the two respiratory states. In curve A, the numbers next to the QRS waves are the classes of the onset of the QRS waves according to the deciles on the RI curve B in which the QRS onset points are located.

Figure 6:
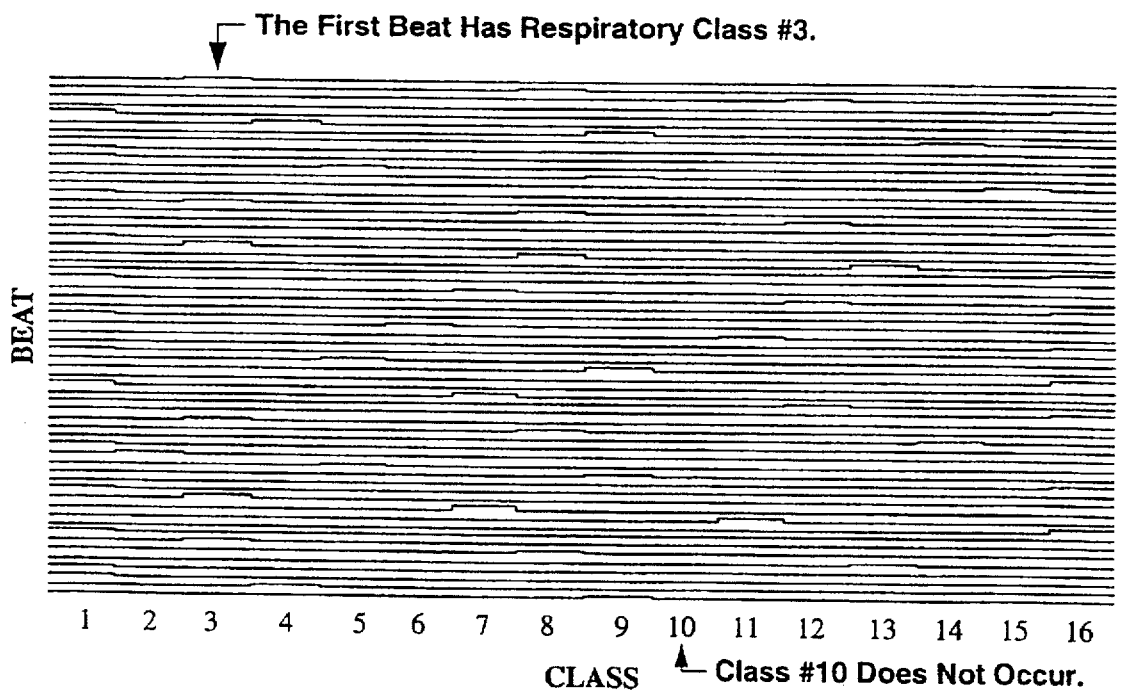
FIG. 6 is a pictorial representation of an example of the R matrix prior to censoring.

FIG. 6 is a pictorial representation of one instance of the raw (not yet censored) R matrix. Censoring will be discussed below. The R matrix, for matrix operations in the above equations, should be a nonsingular matrix. If, due to the way the respiratory cycles are classified and the happenstance of the impedance timeseries upon which the interference matrix is based, there is a respiratory class that does not occur in the timeseries, resulting in the matrix having a column consisting solely of zeros (e.g., class 10 in FIG. 6), the interference matrix can be made nonsingular to obtain the desired nonsingular R matrix, e.g., by dropping the column or by orthogonalization, e.g. by Gram-Schmidt orthogonalization.

Oblique Projection of Normal Data

Figure 7A:
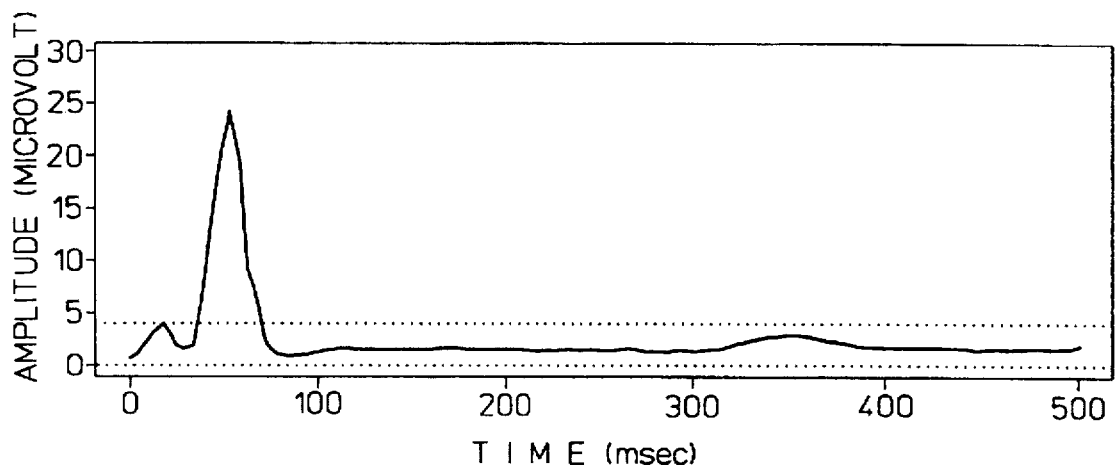
FIG. 7A shows the results of orthogonal projection, the inferred Wenckebach activity for a normal subject.
Figure 7B:
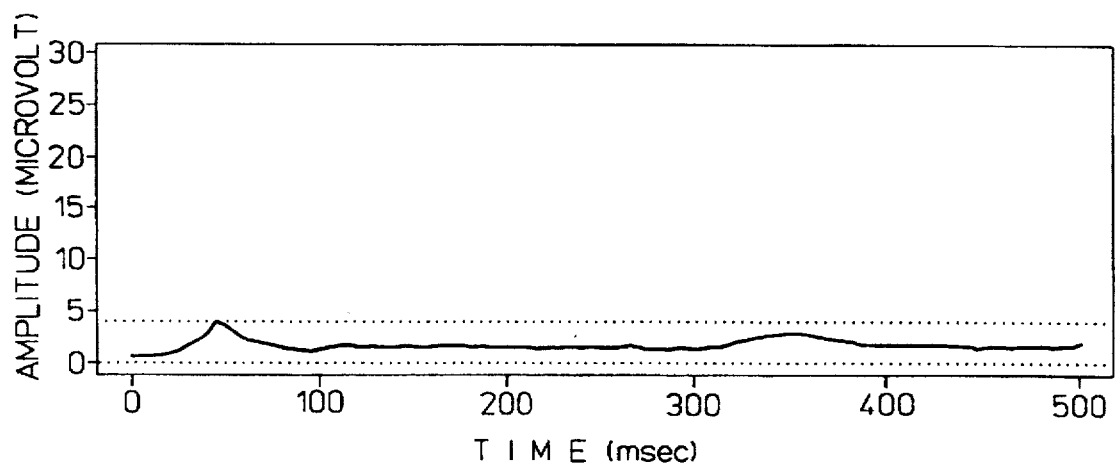
FIG. 7B shows the results of oblique projection, the inferred Wenckebach activity for the normal subject of FIG. 7A.

FIG. 7A shows the results of orthogonal projection and FIG. 7B that of oblique projection, using R matrix for QRS onset, on inferred Wenckebach activity in a normal subject. Although there is still a slight interfering effect in FIG. 7B, it is greatly reduced compared to the result with the orthogonality assumption in FIG. 7A. At their peaks, the oblique projection results are fifteen decibels better than those obtained via orthogonal projection. The residuum of interference is believed to be due to imperfections in beat alignment and leakage of cardiac-filling interference.

Sometimes a beat is too noisy (i.e., over a selected limit) and is preferably omitted. For example, the beat may be noisy because it occurs during a deep breath, or because it is otherwise anomalous. In such cases, when a beat is omitted, R, W, and b should each be properly censored so that the respiratory classes and Wenckebach rhythms correspond to the included beats. This is called "censoring" herein. Various techniques for censoring data to remove abnormal data are known in the art and can be adapted to the present invention.

Figure 8:
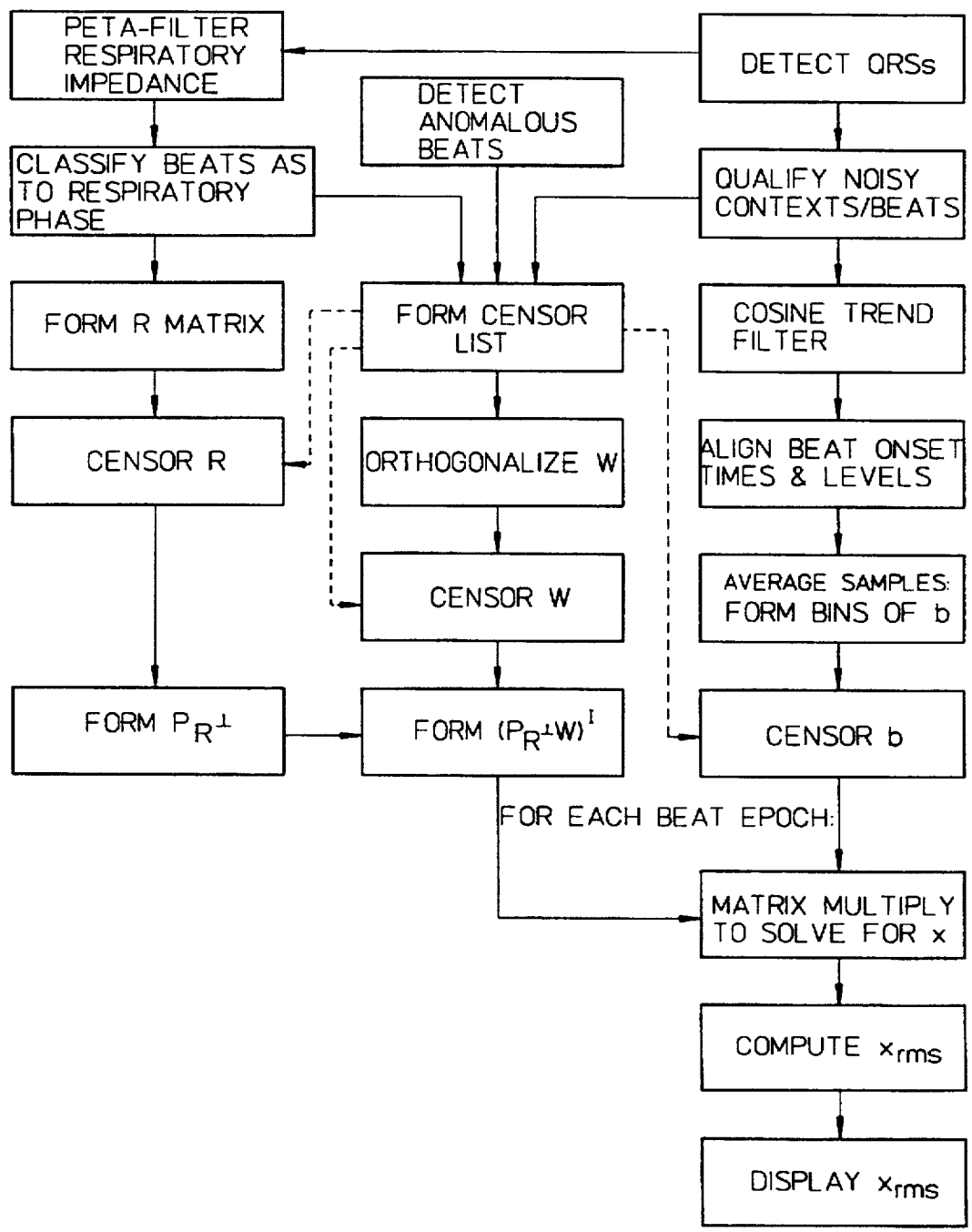
FIG. 8 shows the preferred computational procedures for carrying out the computations of Wenckebach basis function strength according to the present invention.

FIG. 8 shows the preferred procedures for carrying out the computations. Briefly, the respiratory impedance (RI) and the ECG signals are measured. The respiratory impedance (RI) signal is filtered, e.g., with a PETA filter. The data of the filtered RI signal is classified to determine the respiratory phases therein. From the RI data, deep breaths are identified. From the ECG data, excessively noisy beats are identified. These form the bases for censoring-forming a list of the beats to be discarded. The R matrix is formed based on the classified RI data, then orthogonalized (if necessary to remove singularity) and censored. As a result, the matrix $P_R\bot$ is obtained.

From the detected ECG signal, the QRS waves are identified. Also noisy beats and contexts are identified for censoring. The ECG signal data are filtered. A variety of filters can be used. An example of a digital filter suitable for this purpose is the "sinusoidal trend filter" described in U.S. patent application Ser. No. 08/624,194, filed Mar. 28, 1996. The ECG data is arranged to align the beat onset time for the beats and the signal level (i.e., voltage magnitude at the onsets of the QRS's. By selecting a range of time at a particular point of a beat, e.g. for 0.05 second after the QRS onset, and arranging the data in a vector form, the uncensored measurement b is obtained. After censoring to remove the excessively noisy or anomalous beats, the censored b is obtained.

Based on the Wenckebach modes and phases to be evaluated, e.g., the 26 phases of FIG. 2A, an uncensored Wenckebach matrix is formed. This Wenckebach matrix is then orthogonalized to remove singularity, forming a nonsingular Wenckebach matrix W. This orthogonalized Wenckebach matrix is then censored. From $P_R\bot$ and the orthogonalized matrix W, we can form $(P_R\bot W)^I$. The matrix $(P_R\bot W)^I$ can be multiplied with b to solve for x, which is the vector of the Wenckebach basis function strengths. From x, the overall root mean square value $x_{rms}$ can be determined. The $x_{rms}$ can then be displayed to indicate the presence or absence of Wenckebach activity. This provides a method to identify cyclical irregular intramyocardial activity, thereby indicating the risk of SCD.

When the same data (e.g., those associated with FIG. 7) are processed using oblique and using orthogonal projections as in the above method, the results indicate that in normal respiration the oblique method is superior to the orthogonal method. Additionally, to investigate how simulated Wenckebach signals will be detected by oblique projection, we superimposed a pair of fictitious 2:1 Wenckebach signals timed at the ST-T segment and the QRS segment of the heart beat. The results show that the pair of signals is correctly detected when the peak amplitudes of the Wenckebach activity are 80 µV. When the amplitudes of the pair of Wenckebach signals are small, i.e., only 10 µV, the blip due to Wenckebach activity is adequately detected when it occurs during the ST-T segment but is buried in interference when it occurs during the QRS segment. This indicates that the present invention is useful for detecting ST-T alternans. The technique of the present invention is applicable for analyzing for possibly complex intramyocardial Wenckebach activity, i.e., Wenckebach signals with two or more Wenckebach phases. This analysis of 2:1 Wenckebach signals is shown for illustrative purposes only, not as a limit to the scope of application of the present invention. The present technique also is useful for detecting non alternan Wenckebach activity.

Although the preferred embodiment of the present invention has been described and illustrated in detail, it is to be understood that a person skilled in the art can make modifications within the scope of the invention.

APPENDIX

Model studies have shown that "the major cause of the surface potential changes with respiration is due to the change in heart position relative to electrode positions" (See, J. N. Amoore et al., "Respiration and the ECG: A Study Using Body Surface Potential Maps."*J ECG* 21(3):263–271, 1988). Consider the potential produced at a point by a single fixed-position dipole, the classical equivalent cardiac generator, if the radius vector from dipole-i to an electrode A is $r_{Ai}$, the angle between that vector and the dipole direction is $\Theta_{Ai}$, and the dipole strength is $\tau_i$, then the infinite-medium potential at A due to dipole-i is:

$$\Phi_{Ai} = \frac{\tau_i \cos\Theta_{Ai}}{r_{Ai}^2} \qquad \text{Eq. A1}$$

As one breathes in, the cardiac long axis rotates down and forward. Suppose that the dipole rotates due to respiration so that the relevant angle becomes $\Theta_{Ai} + \Delta\Theta_R$,
where $\Delta\Theta_R$ is the amount of rotation, then the perturbed potential will be:

$$\Phi_{Ai}^R = \frac{\tau_i \cos(\Theta_{Ai} + \Delta\Theta_R)}{r_{Ai}^2} = \frac{\tau_i}{r_{Ai}^2} \{\cos\Theta_{Ai}\cos\Delta\Theta_R - \sin\Theta_{Ai}\sin\Delta\Theta_R\} \qquad \text{Eq. A2}$$

As one breathes shallowly, $\Delta\Theta_R$ varies from zero to about ten degrees (0.17 radians). In this small angle regime and to first order, the potential equation simplifies to:

$$\Phi_{Ai}^R = \frac{\tau_i}{r_{Ai}^2} \{\cos\Theta_{Ai} - \Delta\Theta_R \sin\Theta_{Ai}\} = \qquad \text{Eq. A3}$$

$$\frac{\tau_i}{r_{Ai}^2} \cos\Theta_{Ai}\{1 - \Delta\Theta_R \tan\Theta_{Ai}\} = k_{Ai}\Phi_{Ai}$$

where $k_{Ai}$ is the constant of proportionality appropriate to the given phase of respiration, specified by the value of $\Delta\Theta_R$. Thus, when there is shallow respiration and when the single fixed-dipole equivalent generator suffices, then respiration causes proportional changes in the (infinite-medium) potential. For non-limb leads the equivalent cardiac generator needs more degrees of freedom than a single fixed-position dipole provides. A wide variety of equivalent generators has been introduced and studied. For illustrative purposes of this demonstration, a two-dipole generator is assumed. If there are two fixed-position dipoles, i and j, then the total potential at A will be:

$$\Theta^R_{Aij} = k_{Ai}\Theta_{Ai} + k_{Aj}\Theta_{Aj} \text{ not} \propto \Theta_{Aij} \qquad \text{Eq. A4}$$

The lack of proportionality results from the fact that the two constants will almost invariably differ. For the multiple dipole case, we may instead write the infinite-medium potential, as perturbed by shallow respiration, thus:

$$\Phi_A^R = \Phi_A - \Delta\Theta_R \sum_i \frac{\tau_i}{r_{Ai}^2} \sin\Theta_{Ai} \qquad \text{Eq. A5}$$

Therefore, in the shallow respiration case, the perturbed potential is just the uncontaminated potential minus a respiration contamination potential. The shallow-respiration interference is additive.

What is claimed is:

1. An apparatus for detecting repeating patterns of irregular intramyocardial activity in the body of a patient, comprising:
   (a) means for measuring electrocardiographic (ECG) signals from the body;
   (b) means for measuring respiratory signals from the body; and
   (c) a processor electrically associated with the means for measuring ECG signals and with the means for measuring respiratory signals, for numerically reducing interfering effects of respiration on the measured ECG signals, based on the respiratory signals, and for determining the presence or absence of intramyocardial Wenckebach activity.

2. The apparatus according to claim 1 wherein the processor:
   (a) stores data of a nonsingular Wenckebach matrix W corresponding to Wenckebach phases of modes for cardiac activation beats;
   (b) generates a nonsingular interference matrix R corresponding to a relationship of phases of the respiration signals relative to the measured ECG signals; and
   (c) calculates a vector of Wenckebach basis function strengths x based on the nonsingular Wenckebach matrix W, the nonsingular interference matrix R, and the measured ECG signals, the Wenckebach basis function strengths indicating the presence or absence of repeating patterns of irregular intramyocardial activity.

3. The apparatus according to claim 2 wherein the processor calculates the Wenckebach basis function strengths via a relationship describing the measured ECG signals as comprising a-Wenckebach factor and a respiratory interference factor, in said relationship treating amplitude of the measured ECG signals as comprising amplitude of the Wenckebach factor added to amplitude of the respiratory interference factor, and in said relationship the nonsingular Wenckebach matrix W and the nonsingular interference matrix R act on the vector of Wenckebach basis function strengths x to describe the Wenckebach factor, the processor calculating the Wenckebach basis function strengths in terms of the measured ECG signals, of the nonsingular Wenckebach matrix W, and of the nonsingular interference matrix R, the Wenckebach basis function strengths being values that indicate the presence or absence of voltage in the ECG signals caused by repeating patterns of irregular intramyocardial Wenckebach activity.

4. The apparatus according to claim 2 wherein the nonsingular interference matrix R spans an interfering subspace <R> and wherein the processor determines a matrix $P_R\perp$ spanning the orthogonal complement of the interference subspace <R> based on the nonsingular interference matrix R to obtain a matrix of Wenckebach basis function strengths with reduced respiratory interference.

5. The apparatus according to claim 2 wherein the processor divides the respiratory signals into respiration cycles and further divides a respiration cycle into respiratory phases and classifies heart beats from the measured ECG signals based on the respiratory phase each heart beat is in so as to determine the matrix R.

6. The apparatus according to claim 2 wherein the processor orthogonalizes a singular matrix representing Wenckebach phases of modes to remove singularity therefrom to obtain the nonsingular Wenckebach matrix W.

7. The apparatus according to claim 2 further comprising a display device for displaying the Wenckebach basis function strengths to show the presence or absence of Wenckebach activity.

8. The apparatus according to claim 2, wherein the means for measuring respiratory signals comprises electrodes for measuring respiratory impedance signals as the respiratory signals.

9. The apparatus according to claim 2, wherein the processor derives a vector b from the measured ECG signals, including averaging out repetitive components in the ECG signals and calculates the vector of Wenckebach basis function strengths x such that the nonsingular matrix R, the nonsingular Wenckebach matrix W, the vector b derived from the measured ECG signals, and the vector of Wenckebach basis function strengths x are related by: $x=((I-R\ R^I)W)^I b$ where I is the identity matrix and the superscript I represents generalized inversion of the matrix associated therewith.

10. A method for detecting repeating patterns of irregular intramyocardial activity, comprising:
 (a) measuring electrocardiographic (ECG) signals;
 (b) measuring respiratory signals;
 (c) numerically reducing interfering effect of respiration on the measured ECG signals, based on the respiratory signals; and
 (d) determining the presence or absence of intramyocardial Wenckebach activity based on the measured ECG signals while reducing interfering effect of respiration.

11. The method according to claim 10 wherein the step of reducing interfering effect of respiration includes the steps of
 (a) generating a nonsingular Wenckebach matrix W describing phases of modes of Wenckebach activity;
 (b) generating a nonsingular interference matrix R corresponding to a relationship of phases of the respiration signals relative to ECG signals; and
 (c) calculating a vector of Wenckebach basis function strengths x based on the nonsingular Wenckebach matrix W, the nonsingular interference matrix R, and the measured ECG signals, for determining the presence or absence of repeating patterns of irregular intramyocardial activity, the vector of Wenckebach basis function strengths x indicating the intensity of Wenckebach activity in W.

12. The method according to claim 11 wherein the Wenckebach basis function strengths x are calculated via a relationship that describes the measured ECG signals as comprising Wenckebach factor being additive to respiratory interference factor, in said relationship the nonsingular Wenckebach matrix W and the nonsingular interference matrix R act on the vector of Wenckebach basis function strengths x to extract the Wenckebach factor, such that the Wenckebach basis function strengths are expressed in terms of the measured ECG signals, the nonsingular Wenckebach matrix W and the nonsingular interference matrix R, the Wenckebach basis function strengths in x being values that indicate the presence or absence of voltage in the ECG signals caused by repeating patterns of irregular intramyocardial Wenckebach activity.

13. The method according to claim 11, wherein the nonsingular interference matrix R spans an interfering subspace <R>, the method further comprising the step of using the nonsingular interference matrix R to determine a matrix $P_R\perp$ spanning the orthogonal complement of the interference subspace <R> to obtain a matrix of Wenckebach basis function strengths with reduced respiratory interference.

14. The method according to claim 11, further comprising orthogonalizing a singular Wenckebach matrix describing phases of modes of Wenckebach activity to obtain the nonsingular Wenckebach matrix W.

15. The method according to claim 11 wherein the Wenckebach matrix W includes more than two generations of Farey Sequence of Wenckebach patterns.

16. The method according to claim 11 wherein the Wenckebach matrix W includes four to five generations of Farey Sequence of Wenckebach patterns.

17. The method according to claim 11, wherein the nonsingular interference matrix R, the nonsingular Wenckebach matrix W, a vector b derived from measured ECG signals by averaging out monotonous repetitive components therein, and the Wenckebach basis function strengths in x are related by: $x=((I-R\ R^I)\ W)^I b$ where I is the identity matrix and $^I$ represents generalized inversion of the matrix associated therewith.

18. The method according to claim 11, further comprising dividing the respiration signals into respiration cycles and dividing the respiration cycles into respiratory phases and classifying heart beats from the ECG signals based on the respiratory phase each heart beat is in so as to determine the matrix R.

19. The method according to claim 14, further comprising performing orthogonalization on a larger Wenckebach matrix $\tilde{W}$ to obtain the nonsingular Wenckebach matrix W.

20. The method according to claim 10 further comprising filtering the ECG signals with a filter to remove electromagnetic interference.

21. An article of manufacture comprising a program storage medium, tangibly embodying a program code means readable by a computer for causing the computer to analyze for repeating patterns of irregular intramyocardial activity of a patient by numerically determining a vector representing the magnitude of Wenckebach activity based on respiratory signals and electrocardiographic (ECG) signals, the program code means including:
 (a) code means for obtaining a nonsingular Wenckebach matrix W describing phases of modes of Wenckebach activity via basis functions;
 (b) code means for obtaining a nonsingular interference matrix R based on the respiratory signals and the ECG signals of the patient, corresponding to a relationship of phases of the respiration relative to the ECG signals to describe the respiratory interference; and
 (c) code means for calculating Wenckebach basis function strengths via a relationship that describes the measured ECG signals as comprising Wenckebach factor being additive to respiratory interference factor, in said relationship the nonsingular Wenckebach matrix W and the nonsingular interference matrix R act on the ECG signals to extract the Wenckebach factor, the Wenckebach basis function strengths being values that indicate the presence or absence of voltage in the measured ECG signals caused by repeating patterns of irregular intramyocardial Wenckebach activity, the basis function strengths being the components of the vector.

* * * * *